United States Patent [19]

Ganten et al.

[11] Patent Number: 5,731,489
[45] Date of Patent: Mar. 24, 1998

[54] TRANSGENIC RATS CONTAINING AT LEAST ONE HUMAN GENE WHICH PARTICIPATES IN BLOOD PRESSURE CONTROL

[75] Inventors: Detlev Ganten, Tischbeinstr. 5, 6900 Heidelberg, Germany; John Mullins, Edinburgh, Great Britain; Kazuo Murakami, Ibaraki-Ken, Japan

[73] Assignee: Detlev Ganten, Heidelberg, Germany

[21] Appl. No.: 373,495

[22] Filed: Jan. 17, 1995

Related U.S. Application Data

[63] Continuation of Ser. No. 929,375, Aug. 14, 1992, abandoned.

[30] Foreign Application Priority Data

Aug. 14, 1991 [DE] Germany .................. 41 26 968.3

[51] Int. Cl.[6] .................. C12N 15/00; A61K 38/46
[52] U.S. Cl. .................. 800/2; 435/172.3; 424/94.66
[58] Field of Search .................. 800/2

[56] References Cited

FOREIGN PATENT DOCUMENTS 0169672  1/1986  European Pat. Off. .
0247494  12/1987 European Pat. Off. .
0375406  6/1990  European Pat. Off. .

OTHER PUBLICATIONS

Kageyama et al. Biochemistry 23:3603, 1984.
Zeh et al. FASEB 6(4): Abstract A1344, 1992.
Ganten et al. Hypertension 17(6 nts):843, 1991.
Ganten et al PNAS 89:7806, 1992.
Miyazaki et al. PNAS 89:5999, 1984.
Mullins et al Nature 344:541, 1990.
Mullins et al, Fulminant hypertension in transgenic rats harbouring the mouse Ren-2 gene, Nature 344, pp. 541–544, 1990.

*Primary Examiner*—Suzanne E. Ziska
*Attorney, Agent, or Firm*—Birch, Stewart, Kolasch & Birch, LLP

[57] ABSTRACT

The present invention relates to transgenic rats in the genome of which at least one human gene is integrated the gene product of which participates in blood pressure control. More specifically, the invention relates to transgenic rats and their offspring exhibiting increased blood pressure (>90/ >140 mm Hg) or high blood pressure (>95/>160 mm Hg). Finally, the invention relates to processes for the production of the transgenic rats of the present invention and their offspring and their use for pharmacological tests.

15 Claims, 8 Drawing Sheets

HR = heart rate

BP = blood pressure

FIG. 7A

HR = heart rate
BP = blood pressure

TRANSGENIC RATS CONTAINING AT LEAST ONE HUMAN GENE WHICH PARTICIPATES IN BLOOD PRESSURE CONTROL

This application is a continuation of application Ser. No. 07/929,375 filed on Aug. 14, 1992, now abandoned.

The present invention relates to transgenic rats in the genome of which at least one human gene is integrated the gene product of which participates in blood pressure control.

More specifically, the invention relates to transgenic rats and their offspring exhibiting increased blood pressure (>90/>140 mm Hg) or high blood pressure (>95/>160 mm Hg).

Finally, the invention relates to processes for the production of the transgenic rats of the present invention and their offspring and their use for pharmacological tests.

Transgenic animals are genetically modified animals in which at least one foreign gene has been inserted into the genome. These animals allow regulatory processes on the cellular level to be examined and influenced in a systematic and specific manner not achievable with any other test systems. Furthermore, it is possible to test the effect of certain drugs with these transgenic animals and thus to perform preliminary tests for the development of new pharmaceutically active substances.

In the technique for producing transgenic animals which was developed first and which is the most widely spread, fertilized oocytes are firstly taken from female animals. The desired foreign DNA (the "transgene") is then incorporated into the oocytes. Several methods are available which differ in their principle: on the one hand the transgene can be incorporated into the oocytes and thus into the genome via an appropriate retroviral vector, on the other hand by microinjection (Palmiter R. D., Brinster R. L.: Germline transformation of mice. Ann. Rev. Genet. 20 (1986), 465–499). Recombinant retroviral vectors are incorporated into the oocytes according to processes known from the prior art (Jaenisch R.: Transgenic animals. Science 240 (1988), 1468–1475). In the microinjection technique the cloned foreign DNA is injected directly into one of the two *pronuclei* of a fertilized oocyte prior to the fusion of the *pronuclei* of sperm and oocytes. The oocytes are then reimplanted into pseudopregnant females for gestation.

Transgenes can also be incorporated into embryonic, fetal or adult pluripotent stem cells (Capecchi M.: Altering the genome by homologous recombination. Science 244 (1991) 1288–1292). Embryonic stem cells can be isolated from blastocysts cultivated in vitro and can be kept stable in culture over many cell generations, i.e. without any differentiation. Foreign DNA, e.g., can be incorporated into the embryonic stem cells by electroporation. After selection of stem cells which carry the desired foreign DNA the former are injected into the inner cell mass of blastocysts. The blastocysts are then implanted into pseudopregnant females. Since not all the cells of the inner cell mass of the blastocysts carry the transgenes, the animal developing therefrom is chimeric with respect to the transgenes. Due to the pluripotency of the stem cells all tissue species and thus also the germ cells may carry the transgenes. By subsequent crossbreeding of the chimerae, animals are obtained in which all the cells carry the transgenes. Conventional microinjection techniques of fertilized oocytes and the route over embryonic stem cells for the production of transgenic animals exhibit both practical and methodological advantages and disadvantages. The choice of the technique to be employed mainly depends on the object to be attained by the experiment and on the technical possibilities of the individual laboratory.

The specific advantage of the microinjection technique is that the method is well established and relatively easy to perform. When appropriate genomic gene constructs with the respective promoters are selected a target-orientated gene expression can be obtained. However, in general it can be expected to express the endogenous gene and the transgene. Correspondingly, interferences between the two gene products may occur which make an evaluation of the test results difficult. A further advantage of the microinjection technique is that it is relatively easy to inject several genes at one time so that the overall expression of the gene products can possibly be increased and the manifestation of the phenotype improved.

The main advantage of the embryonic stem cell technique is that the cells transfected with the transgene can be tested prior to reimplantation for integration and the effect of the transgenes. In contrast to the conventional microinjection technique the respective endogenous gene can be removed from a chromosome by homologous recombination with the transgene. By subsequent crossbreeding experiments animals can be bred which carry the transgene on both chromosomes. If mutations are incorporated into the transgenes which block expression of the normal gene product, the endogenous genes can be eliminated by this technique and functional studies can thus be performed.

The methods for the production of transgenic animals as described above in combination with conventional genetic engineering methods provide unexpected new possibilities for creating in vivo animal models for the detection of disease processes and on the basis of this for the development of new drugs. Two prerequisites have to be fulfilled in order for a new generation of etiotropic drugs to be developed:

1) the pathophysiological causes of the disease to be treated must be known; and
2) experimental models must be available which allow examination of the therapeutic effectiveness and the specificity of substances in an as easy as possible manner and with a high as possible expressiveness.

One of the disease processes which can be researched more thoroughly in such animal models is the one leading to increased blood pressure (i.e. to values which exceed the limit of normal of 90 mm Hg diastolic and 140 mm Hg systolic) and to high blood pressure (values exceeding 95 mm Hg diastolic and 160 mm Hg systolic).

High blood pressure (hypertension) is classified in humans in primary and secondary forms. Secondary forms of hypertension have known causes but account for only a small percentage of the total of hypertensive patients. In contrast, primary hypertension is a widespread disease from which 20% of the adult population suffers. Its causes are unknown. However, it is assumed that there may be a hereditary component which results from the interaction of various genes which participate in blood pressure control. The presently available therapies therefore mostly do not have causal but symptomatic effect and carry numerous side-effects.

In the regulation of the blood pressure the renin angiotensin system (RAS) plays an important role together with the central nervous system, the kidneys and hormones such as vasopressin (AVP), atrial natriuretic factor (ANP) or aldosteron. By way of the effector peptide angiotensin II the RAS is involved in the control of the peripheral vascular resistance and the maintenance of the electrolyte and liquid homeostasis. It is said to have causative importance for the genesis of various forms of renal high blood pressure. A pathogenetic part in the development of primary hypertension is discussed (Ganten D., Ritz E., Lehrbuch der Hypertonie—Pathophysiologie, Klinik, Therapie, Epidemiologie, Stuttgart, New York: Schattauer Verlag, 1985).

Human angiotensinogen is a hormone precursor molecule having a molecular weight of 61,000. It consists of a single polypeptide chain. The DNA and amino acid sequence of the molecule are known (Fukamizu et al., Biochem. Biophys. Res. Comm. 165 (1989), 826–832). The angiotensinogen gene which belongs to the super gene family of the protease inhibitor genes is expressed in the liver and the thus obtained angiotensinogen is discharged into the blood where it is digested by the enzyme renin (EC 3.4.23.15.), an aspartyl proteinase. Renin (Miyazaki et al., Proc. Natl. Acad. Sci. USA 81 (1984), 5999–6003) is synthesized, accumulated and excreted by the glomerular cells of the juxtaglomerular system of the kidneys. In the blood renin cleaves angiotensinogen into the N terminal dekapeptide angiotensin I and in a 450 amino acid polypeptide, des-(angiotensin I)angiotensinogen. Angiotensin I upon contact with the vascular endothelium is transferred by the ubiquitous conversion enzyme (CE) into the physiologically active, multifunctional octapeptide angiotensin II.

The circulating angiotensin II, plasma angiotensin II, mediates via specific receptors a multitude of physiologic effects such as contraction of the unstriped vascular muscles, release of aldosteron in the suprarenal cortex, direct sodium and water retention in the kidneys and a subsequent increase in blood pressure. Angiotensin II likewise stimulates the appetite for salt and thirst and has important effects on the activity of the autonomic nervous system and on the release of pituitary hormones. Besides the formation of angiotensin II (ANG II) in the plasma (hormonal RAS), the formation of angiotensin II in the tissue (tissue RAS, paracrinic RAS) likewise plays an important role. Local angiotensin II formation has been detected in particular in the brain, in the suprarenal cortex, in the heart and in the vascular walls (Ganten D., Lindpaintner K., Ganten U., Peters J.: Transgenic rats: New animal models in hypertension research. Hypertension 17 (1991), 843–855. Lindpaintner K., Ganten D.: The cardiac renin-angiotensin system. An appraisal of present experimental and clinical evidence. Circ. Res. 4 (1991), 905–921. Schelling P., Fischer H., Ganten D.: Angiotensin and cell growth: A link to cardiovascular hypertrophy? J. Hypertens. 9 (1991), 3–15). A participation of the above tissue angiotensin II in blood pressure control was shown in several studies. The anti-hypertensive effect of the inhibitors of RAS in normal or even reduced plasma RAS is also a pointer to the functional significance of local angiotensin synthesis.

The degradation of angiotensin II into inactive peptides is performed by angiotensinases. The physiological activity of the renin-angiotensin system is mainly controlled via the control of the secretion rate of renin and thus the formation rate of angiotensin II. The short plasma half-life of renin and the quick release from storage tissue allows a quick adaption to changing physiological and pathophysiological conditions. The control mechanisms of renin thus play a prominent role in blood pressure control.

Specific inhibitors of renin therefore play a key role in the causal therapy of hypertension. So far such developments can be carried out almost exclusively by using primates since the renin is highly species-specific, i.e. renin inhibitors which have been developed for humans react only with human or primate renin and not with renin of other species. This fact results in many difficulties in the development of new blood pressure controlling substances which can only be overcome by conventional methods which are very time-consuming.

For the further research of RAS transgenic animals containing the components of RAS have already been produced, namely transgenic mice into the genome of which the human renin gene (Fukamizu et al., loc. cit.), the rat renin gene and/or the rat angiotensinogen gene (Ohkubo et al., Proc. Natl. Acad. Sci. USA 87 (1990), 5153–5157) has/have been introduced. Furthermore, transgenic rats are known which express the mouse Ren 2-renin gene (Mullins et al., Nature 433 (1990), 541–544). Expression of the renin and angiotensinogen genes in these animals was tissue specific provided they were controlled by the homologous promoter. Fukamizu et al. have not performed studies on the effect of transgenic expression on the blood pressure. The works of Mullins et al. have shown that despite reduced renin values in the plasma and in the kidneys an increase in blood pressure may occur. A clear correlation between the effect of the RAS components and the increase in blood pressure could not be shown. In the system chosen by Ohkubo et al. an interpretation of the data is difficult and does not lead to unequivocal results since it is known that mouse renin cleaves rat angiotensinogen but that rat renin does not cleave mouse angiotensinogen.

The ideal model system in which only the expression products of the transgenes react with each other and allow an unequivocal causal correlation to be drawn between the activity of gene products which participate in blood pressure control and the change of the blood pressure is not known from the prior art. However, only such a model system fulfils the above mentioned prerequisites for the development of a new generation of drugs having causal effect on the high blood pressure. In such a preferred model system only the expression products of human genes interact the gene products of which participate in blood regulation.

The technical problem underlying the present invention is therefore to provide model systems which allow genes and gene products participating in blood pressure control of humans to be examined in a manner which is specific for humans.

The above technical problem is solved by the provision of the embodiments characterized in the patent claims.

The subject matter of the invention is a transgenic rat the genome of which contains at least one expressible human gene the gene product of which participates in blood pressure control. Preferably, the transgenic rat can be used to perform invasive chronic instrumentations and hemodynamic as well as endocrinological analyses.

The term "transgenic" means that one or several additional genes is/are integrated into the genome.

The term "rat" relates to animals which from the point of systematic zoology belong to the genus Rattus.

The transgenic animal model according to the invention was developed exemplarily for the species *Rattus norvegicus* (to obtain fertilized oocytes rats of the laboratory strains Sprague Dawley and Wistar Kyoto were mated) but it can be generated by any other species of the genus Rattus, e.g., of the species *Rattus rattus*.

The term "expressible" means that the gene can be transcribed and the thus obtained mRNA translated resulting in a gene product which can perform its physiological function. An expressible gene is therefore provided with all necessary control sequences.

The term "genome" of a rat relates to its entire hereditary information. The latter is localized on the chromosomes of all cells, i.e. of the somatic and the germ cells.

The term "blood pressure control" relates to the adjustment of the blood pressure to a normal value. The latter for humans is 90 mm Hg diastolic and 140 mm Hg systolic. Values of >90 and ≦95 mm Hg diastolic and >140 and ≦160 mm Hg systolic are considered to be "increased blood pressure". According to the definition of WHO "high blood pressure" is reached if the values exceed 95 mm Hg diastolic and 160 mm Hg systolic.

The term "invasive chronic instrumentations" relates to the chronic implantation of catheters into arteries, veins, ureters and also intracerebroventricularly. These catheters allow exogenous substances to be infused and at the same time the effects obtained to be measured.

The term "hemodynamic as well as endocrinological analyses" relates to the measurement of hemodynamic parameters after catheter implantation which influence blood pressure control as well as to the determination of cardiovascular and renal functional values in connection with the effect of the transgene (transgenes) (hemodynamic analysis) and to the collection of blood in order to determine the interactions of the transgene (transgenes) or the gene product(s) and other hormonal systems participating in blood pressure control (endocrinological analysis).

In an embodiment of the rat according to the invention its genome contains at least two expressible human genes the gene products of which participate in blood pressure control.

In a further embodiment of the transgenic rat according to the invention at least one of the genes is controlled by a homologous promoter.

A "homologous" promoter relates to a promoter which controls the expression of the gene under natural conditions.

In another embodiment of the transgenic rat according to the invention at least one of the genes is controlled by a heterologous promoter.

The term "heterologous" means that the gene is not controlled by its natural promoter but by a promoter which under natural conditions controls the expression of another gene.

If the rat of the present invention contains more than one human gene in its genome the gene product of which participates in blood pressure control, all genes can be controlled by homologous promoters. In another embodiment all human genes are controlled by heterologous promoters. In a further embodiment the various human genes are controlled either by homologous or heterologous promoters as required.

In a preferred embodiment of the transgenic rat of the present invention the gene or at least one of the genes codes for renin.

In a further preferred embodiment of the transgenic rat of the present invention the gene or at least one of the genes codes for angiotensinogen.

In a most preferred embodiment the genome of the transgenic rat of the present invention contains at least one gene coding for renin and at least one gene coding for angiotensinogen.

In a further most preferred embodiment the transgenic rat of the present invention exhibits a blood pressure increased by the gene(s) which has/have been introduced, preferably exceeding 90 mm Hg diastolic and 140 mm Hg systolic or a high blood pressure caused by said gene(s), preferably exceeding 95 mm Hg diastolic and 160 mm Hg systolic.

A further object of the invention is a method for producing a transgenic rat carrying the human renin and/or the human angiotensinogen gene in which the gene(s) is/are introduced into the rat or its ancestors not later than at the eight-cell stage.

The term "eight-cell stage" is to be understood as the stage after three divisions of the fertilized oocyte during embryonic development. In the so-called morula stage all eight cells are still pluripotent, i.e. they can develop into all tissue types including germ cells. After a further division, i.e. at the "sixteen-cell stage", they are no longer pluripotent.

A further object of the invention is the use of the transgenic rat of the invention for pharmacological tests on blood pressure control.

Examples for such pharmacological studies are tests which are used to measure the influence of inhibitors specific for human renin on the blood pressure of the transgenic rats of the invention. The rats can be subjected to a diet low in sodium before administering the inhibitor. In further examples of such pharmacological tests the effect of angiotensin receptor antagonists, e.g., DUP 753 on the blood pressure of the transgenic rats of the present invention can be determined.

The Figures show:

Plasmid pHRgTM15 contains the entire human renin gene (10 exons and 9 introns) including 3 kb of 5' flanking and 1.2 kb of 3' flanking sequence (thick lines) cloned into the plasmid vector pUC19 (thin lines). pUC19 was modified for the cloning process such that its ends were provided with a BglII linker and a ClaI linker after cleavage with KpnI.

Plasmid pHAgTM14 contains the entire human angiotensinogen gene (5 exons and 4 introns) including 1.1 kb of 5' flanking and 2.4 kb of 3' flanking sequences (thick lines) cloned into the plasmid vector pUC19 (thin lines). pUC19 DNA was cleaved by BamHI and provided with NheI linkers.

FIG. 3: RNase Protection Assay Analysis of the Gene Expression of Human Renin (hREN) and Human Angiotensinogen (hAOGEN) in Transgenic Rats a) Expression of human renin mRNA in various tissues of renin transgenic rats.

Abbreviations: P: uncleaved cDNA probe for human renin (cf. Example 1); T: tRNA; KITG-: rat kidney RNA from transgent negative litter mates (negative control group); KI: kidneys; LI: liver; LU: lungs; HE: heart; SP: spleen; GI: gastrointestinal tract; PA: pancreas; SM: mandibular gland; BR: brain.

For electrophoresis 50 µg of whole RNA were applied in each slot.

b) Tissue-specific expression of human angiotensinogen mRNA in angiotensinogen-transgenic rats Abbreviations: cf. a), above; P: uncleaved cDNA probe for human angiotensinogen (cf. Example 2).

For electrophoresis 50 µg whole RNA were applied in each slot with the exception that 5 µg liver whole RNA were applied.

Rat liver RNA from transgene negative litter mates (LITG-) served as a negative control.

FIG. 4: In Situ Hybridization and Immunohistological Chemistry of Renin and Angiotensinogen Gene Products in Tissue of Transgenic Rats Upper row (a, b): renin mRNA expression in renin transgenic rats Expression was determined using a $^{35}S$ labelled probe specific for human renin (a) or mouse renin (b) in subsequent slices of the same tissue block. The probe specific for mouse renin mRNA cross-hybridizes by almost 100% with rat renin mRNA and therefore detects endogenous rat renin transcripts. The probe specific for human renin cross-hybridizes by only 60% with rat renin mRNA. The use of both probes shows exclusively renin transcripts in the region of the glomerular afferent arteriole (arrows). This result points to a tissue-specific expression of both genes in renin producing cells of the kidney, these genes being controlled by their natural promoters.

middle row (c, d): immunohistological chemistry of the renin protein in the kidney of a renin transgenic rat The immunohistochemical data was determined using specific antibodies for human renin (c) (Galen et al., J. Biol. Chem. 254 (1979), 4848) or for rat renin in subsequent slices of the same tissue block. Both antibodies recognize their substrate only in granular extraglomerular cells (arrows) although the reaction of the antibodies was not completely species-specific.

Microscopic magnification of the illustrations a to d is ×440.

lower row (e): angiotensinogen mRNA expression in the liver of an angiotensinogen transgenic rat The result was obtained by using a radioactively labelled probe specific for human angiotensinogen (cf. Example 2) (0.05 mg antisense RNA per tissue slice, duration of exposure 8 days). A high density of the silver grains was exclusively detected in parenchyma cells.

L: lumen of main vein.

(f): angiotensinogen mRNA expression in the liver of a non-transgenic Sprague Dawley rat For detection of angiotensinogen mRNA a probe specific for rat angiotensinogen was used. Otherwise, the test conditions were the same as for (e). The tissue slice was considerably less stained than in (e). Additional control experiments showed that both probes generate a similar signal intensity if they are hybridized with rat and human angiotensinogen transcripts.

Microscopic magnification of illustrations e and f is ×660.

FIG. 5: Reaction of Human and Rat Renin to Stimulation of RAS by Sodium Depletion in Renin Transgenic Rats Diagram a) shows that the amount of human renin in the plasma significantly increases after sodium depletion when furosemide is administered. The value for human renin in the plasma of the transgenic rats prior to sodium depletion is 4.9 pg/ml and is thus in the same range as in the human plasma. After sodium depletion the value for human renin in TGR (hREN) 1936 transgenic rats increases to more than 50 pg/ml when furosemide is administered. As control groups non-transgenic rats were used which did not experience stimulation to express human renin.

Diagram b) shows that the values for endogenous renin in the plasma of both transgenic and non-transgenic rats increase by a factor of 6 after sodium depletion. A comparison of the amounts of endogenous and transgenic renin in the plasma of transgenic and non-transgenic rats shows that the values do not differ significantly prior to or after sodium depletion and thus do not depend on the presence of a transgene.

FIG. 7 Effect of the Administration of Human Renin, Rat Renin, RO425892 and DUP 753 on the Blood Pressure of Angiotensinogen Transgenic Rats Illustration of the blood pressure and heart rate of a conscious free-moving angiotensinogen transgenic rat.

A: the blood pressure increases to plateau levels of 200 mm Hg systolic after infusion of purified human renin which is administered intravenously in a dosage of 5 µg ANG I/ml/h as bolus over a period of 5 minutes. Intravenous administration of RO 425892 in a concentration of 1000 µg/kg body weight reduced the blood pressure to the normal value prior to the treatment within a short period of time.

B: the infusion of renin obtained from rat kidneys likewise results in an angiotensinogen transgenic rat in a rapid increase in blood pressure to a value of about 200 mm Hg systolic. Injection of RO425892 in a concentration of 1,000 µg/kg body weight does not result in a reduction of the blood pressure. Intravenous administration of 10 mg of the angiotensin receptor antagonist DUP 753 per kg body weight as bolus over a period of 5 minutes results in a reduction of the blood pressure to the normal value prior to the treatment.

The test was performed for 48 hrs after implantation of chronic catheters into the femoral artery and vein. Implantation of the catheter did not lead to an increase in blood pressure. The blood pressure was measured with a Senso Nor 840 converter, Horten Electronics, Norway, which was connected to a Hellige Polygraph Recomed 330 P.

The heart rate dropped by about 20–50 beats per minute in a counter-regulatory movement to the increase in blood pressure; the arterial hypertension is therefore not the result of a heart-rate dependent increase in the cardiac output.

FIG. 8: Effect of the Administration of Human Renin and of RO425892 on the Blood Pressure of Angiotensinogen Transgenic Rats A: steady state—blood pressure values in angiotensinogen transgenic rats (dark columns) and non-transgenic litter mates (light columns) before and 10 minutes after bolus injection of purified human renin and inhibitor RO 425892 specific for human renin. As a reaction to the administration of human renin the blood pressure values are substantially increased in transgenic rats but not in non-transgenic rats. The administration of RO 425892 leads to a reduction of the blood pressure to normal values in transgenic rats while in non-transgenic rats no effects on the blood pressure are observed.

B: determination of ANG II plasma values in angiotensinogen transgenic rats.

The plasma values for ANG II were determined during the experiment described under A, above. Production of ANG II is parallel to the increase in blood pressure. Infusion of human renin does not change the ANG II values in non-transgenic rats. This result proves the species specificity of the RAS components examined in this test. The formation of ANG I substantially coincides with the formation of ANG II.

The values are given as median values±SEM (Standard Error of the Mean) with n=6 for each group. The statistical analysis was performed by way of ANOVA. *** means P<0.001. The dosages of the substances used for the infusions are indicated in the legend to FIG. 7.

The methods for the determination of the ANG II values have been described by Schelling et al., Neuroendocrinology 31 (1980), 297–308 and in Hermann et al., Clin. Chem. 34/6 (1988), 1046–1051.

The transgenic rats of the present invention open up new unprecedented possibilities for the research of blood pressure. Tests with transgenic laboratory animals have up to now mainly been performed with mice. A reason for this was that the production of transgenic rats involved substantial technical difficulties linked with the superovulation and the vitality of the oocytes. Rats offer substantial advantages for the research of cardiology as compared to mice: for one thing, they are more suitable for analytic and functional tests due to the availability of techniques of blood pressure measurement which are not applicable in mice. Furthermore, it is virtually impossible to perform chronic follow-up observations of the development of blood pressure in mice. Acute tests using invasive methods harbor great instrumental and methodological difficulties and in general lead to the death of the animals after the tests. Endocrinologic studies inter alia are only possible to a limited extent due to the difficulty of obtaining sufficient amounts of blood. In addition, by far the most comparative pathophysiological and pharmacological data is available for rats in connection with the cardiovascular system. Even more important, however, is the fact that rat models are available both for the secondary and the primary genetically related form of hypertension, the most widely known strains being the spontaneously hypertensive SHR rats. The methodology for the examination of acute and chronic changes of the cardiovascular function of rats, endocrinological, pharmacological, pathophysiological and electrophysiological methods of examination are very well developed and are available for use. Therefore, rats are particularly useful for the development of new drugs for cardiovascular diseases. Furthermore, high blood pressure in rats is defined in the same way as for humans for conventional reasons. Besides, there are no differences with respect to blood pressure values between humans and rats.

With the transgenic rats of the present invention it is possible for the first time to directly correlate changes in blood pressure with the effect of certain expression products of genes, the gene products of which participate in blood pressure control. Surprisingly, it could be shown in the present invention that human renin and human angiotensinogen do not interact with rat renin and rat angiotensinogen. Since it was known from the prior art that rat RAS gene products cross-react with mouse RAS gene products (Mullins et al., loc. cit., Ohkubo et al., loc. cit.) it could be expected that the human RAS gene products interact with rat RAS gene products. The transgenic rats of the present invention therefore exhibit a substantial unexpected advantage vis-à-vis the transgenic rats and mouse known from the prior art which carry the RAS specific genes in their genome as well as vis-à-vis the spontaneously hypertensive rats (SHR) exhibiting genetic high pressure. While the high blood pressure in the SHR system is due to the interaction of gene products of approximately 4 to 8 rat genes and thus at best analogous conclusions for high blood pressure in humans can be drawn, the increased blood pressure of the transgenic rats according to the invention is due to the interaction of only two (human) gene products. The transgenic system of the present invention is thus not disturbed in its expressiveness by the influences of endogenous gene products.

The transgenic rats of the present invention can carry a human gene in their genomes, the gene product of which participates in blood pressure control or several such genes. For example, they can carry only the human renin gene, only the human angiotensinogen gene or both human genes in their genomes. They can be either homozygous or heterozygous for the individual genes. If they only carry one of the human genes in their genome, the gene product of another human gene, this gene product participating in blood pressure control, can be administered to the rat, e.g, by infusions. If the rat exhibits, e.g., the human renin gene, human angiotensinogen can be introduced into the blood circulation of the rat by infusions. Conversely, angiotensinogen transgenic rats can be provided with human renin from external sources. If the transgenic rats of the present invention carry both human genes in their genomes, they can be homozygous or heterozygous for both genes or only for one gene.

Both the renin transgenic rats and the angiotensinogen transgenic rats exhibit roughly the same high and preferably increased values of the transgenic products in the plasma as compared to the values in human plasma. The expression of the two transgenes is tissue specific. The activity of the transgenic renin can be inhibited by an inhibitor specific for human renin.

The renin transgenic rats do not exhibit increased blood pressure A blood pressure dependent on human RAS occurs only if external human angiotensinogen occurs in the blood flow. The angiotensinogen transgenic rats do not exhibit increased blood pressure which, however, can be produced by infusion of human renin. After combination of both human transgenes in the genome of a rat the blood pressure becomes partly dependent on the human transgenic RAS. Such a combination can be achieved by, e.g., cross-breeding renin transgenic rats with angiotensinogen transgenic rats or by microinjection of both human genes into a fertilized oocyte.

The well-being and the general expectation of life of the transgenic rats is not impaired by the transgenic gene products. Since, as explained above, human renin and human angiotensinogen do not react with the corresponding rat RAS components, only the animals carrying both transgenes exhibit a blood pressure depending on the human RAS. The transgenic gene products are furthermore generally endogenous products. Due to their primordium already in the oocyte they do not prompt immunological side-effects.

The use of the transgenic rats of the present invention for testing e.g. pharmacological hypotensive substances, animal tests on higher species, e.g., monkeys, but also on volunteers (human) can be considerably restricted or are rendered unnecessary. At the same time the development costs for new drugs in the blood pressure sector are substantially reduced.

The transgenic test systems of the present invention as compared to the conventional in vitro preliminary tests additionally permit a quicker and more reliable development of blood pressure regulators and thus have a high practical value for the development of improved and more specific drugs. For example, it can be expected that the improvement in the development of renin inhibitors which has become possible with the transgenic rats of the present invention will be reflected in optimized possibilities of therapy of high blood pressure.

Furthermore, the transgenic rats of the present invention allow new approaches in the elucidation of the pathophysiological causes of high blood pressure in the animal model. Thus drugs for the causal treatment of high blood pressure which are specific for humans can be developed in the animal model.

The Examples serve to illustrate the invention.

EXAMPLE 1

Production of Transgenic Rats Carrying the Human Renin Gene in Their Genomes

Figure 1:
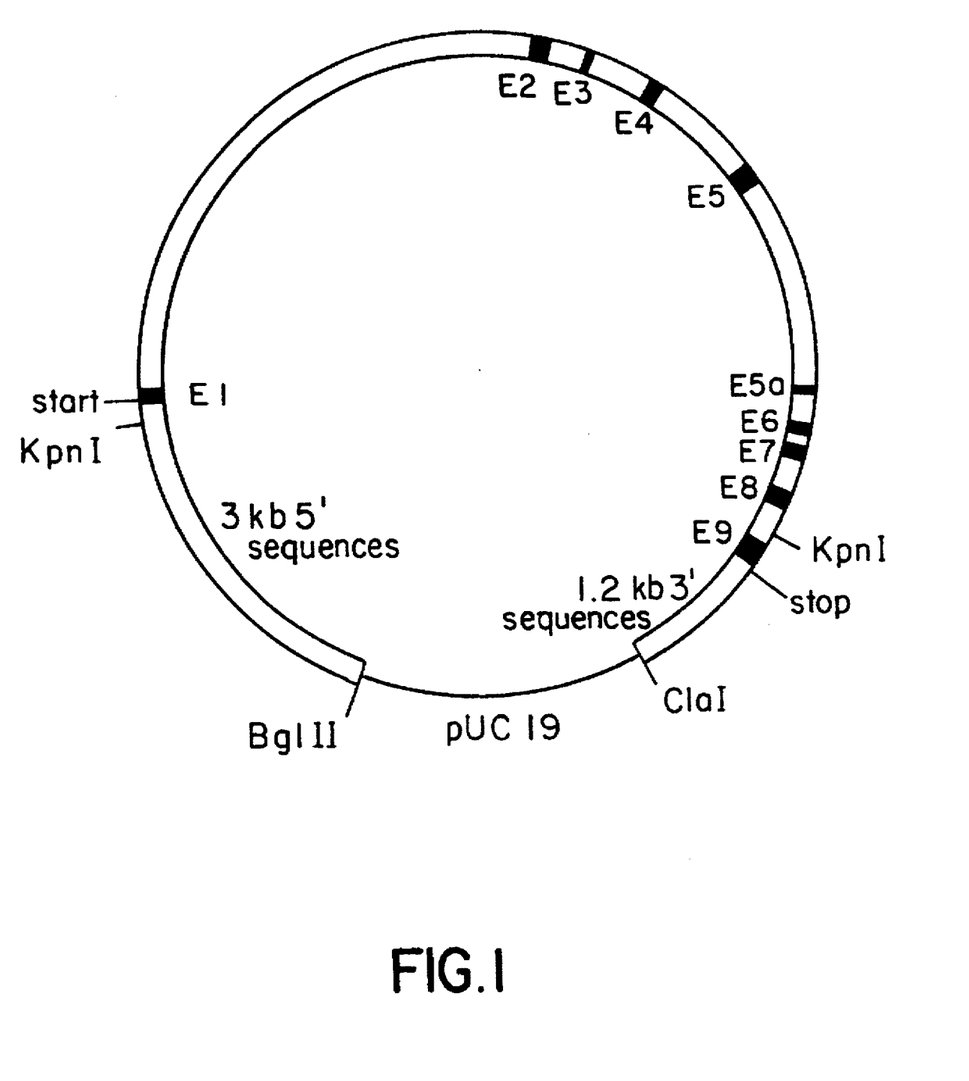
FIG. 1: Restriction Map of Plasmid pHRgTM15

A 17.6 kb DNA fragment encompassing the entire human chromosomal renin gene (10 exons and 9 introns, Miyazaki et al., loc. cit.) including 3 kb of 5' flanking sequence with possible regulatory sequences including the promoter and 1.2 kb of 3' flanking sequence were cloned in a modified pUC19 plasmid vector (FIG. 1) as described by Fukamizu et al., loc. cit.

After amplification of the recombinant DNA and subsequent purification (Sambrook et al., Molecular Cloning, 2nd ed. 1989, Cold Spring Harbor Laboratory, Cold Spring Harbor) the renin gene was separated from the vector DNA by digestion with restriction endonucleases (BglII, ClaI). The linearized renin gene was injected into male *pronuclei* of fertilized oocytes according to the method of Gordon et al., Proc. Natl. Acad. Sci. USA 77 (1980), 7380–7384. Sprague Dawley (outbred) rats were mated with Wistar Kyoto (inbred) rats and the fertilized oocytes were harvested for the injections.

87 injected oocytes were reimplanted into female pseudopregnant Sprague Dawley rats (own breed) according to the method described by Hogan et al., in "Manipulating the mouse embryo", (1986) (editor: Hogan), The Cold Spring Harbor Laboratory, Cold Spring Harbor. 15 offspring were carried to full term and examined for the presence of the transgene. The newborn rats were biopsied and tissue samples were taken from the tail and DNA was isolated according to standard techniques. The DNA was partly digested with the restriction enzyme PvuII and separated by electrophoresis on a 0.8% agarose gel. After transfer of the DNA to a membrane filter (E. Southern, J. Mol. Biol. 98 (1975) 503) the DNA was subjected to hybridization with a probe specific for human renin, a radioactively labelled 300 base pair (bp) fragment of the cDNA clone pDDID2 (Field et al., Hypertension 6 (1984), 597) according to the method by Feinberg and Vogelstein (Sambrook et al., loc. cit.) under stringent conditions and subsequently washed and subjected to autoradiography under stringent conditions. The DNAs of two of the offspring were found to have the hybridization signals of the expected length which are specific for human renin. This means that two of the offspring carry the human renin transgene in their genomes. These animals were designated with TGR (hREN) 1936 and TGR (hREN) 1988. Both animals transmitted the transgene to their offspring by heredity. In the line derived from TGR (hREN) 1936 the transgene in the F3 generation is present in homozygous form.

EXAMPLE 2

Production of Transgenic Rats Carrying the Human Angiotensinogen Gene in Their Genomes Genomic DNA was isolated from human placental tissue according to the method described by Blin and Stafford, Nucleic Acids Res. 3 (176), 2303. According to standard techniques (Sambrook et al., loc. cit.) the DNA was cloned in the phage Charon 28 after partial digestion with the restriction enzyme Sau 3A. About 6×10⁵ recombinant phages of this gene library were plated and were screened with a 1262 bp BstEII fragment which was isolated from Phag3 (Kageyama et al., Biochemistry 23, (1984) 3603–3609) as probe for the angiotensinogen gene.

The recombinant phage DNAs were transferred to membrane filters according to standard techniques (Sambrook et al., loc. cit.) and hybridized with the probe at 65° C. for 16 hrs.

As a buffer a 5×SSPE solution (1×SSPE=0.15M NaCl, 0.01M NaH$_2$PO$_4$·H$_2$O, 1 mM EDTA, pH 8.4), 1×Denhardt's solution (0.02% BSA, 0.02% polyvinylpyrrolidone, 0.02% Ficoll), 0.01% SDS, 100 µg/ml denatured salmon sperm DNA, 5×10⁶ cpm/ml radioactively labelled probe were used. After hybridization, the filters were washed twice with 2×SSC (1×SSC=0.15M NaCl, 0.015M sodium citrate, pH 7.0) at room temperature and twice with 2×SSC and 0.1% SDS at 65° C. for 30 min. The filters were dried and subjected to autoradiography at −70° C.

The 3.5 kb EcoRI/BamHI, 5.0 kb BamHI and 0.5 kb BGIII fragments from the recombinant phage IhAG-1 exhibiting a hybridization signal with the probe were subcloned into the polylinker region of the plasmid vector pUC19 at appropriate sites. The respective recombinant plasmids were designated phAG35EB, phAG50b and phAG85G. The genomic 2.7 kb BamHI fragment from phAG85G was cloned into the BamHI site of pUC19. The recombinant plasmid was designated phAG272B.

The structure of the human angiotensinogen gene was elucidated:

Exon carrying DNA fragments and the 5' and 3' flanking regions were identified by restriction mapping. After subcloning into M13 or pUC19, the primary structure of the exons, the exon/intron junctions and the flanking regions were sequenced by the chain termination method (Sanger al., Proc. Natl. Acad. Sci. USA 74 (1977) page 5463).

The nucleotide sequences of all exon-intron junctions were determined. The human angiotensinogen gene is composed of 5 exons and 4 introns, which could be proven by comparison with the known cDNA sequence (Kageyama et al., loc. cit.).

Figure 2:
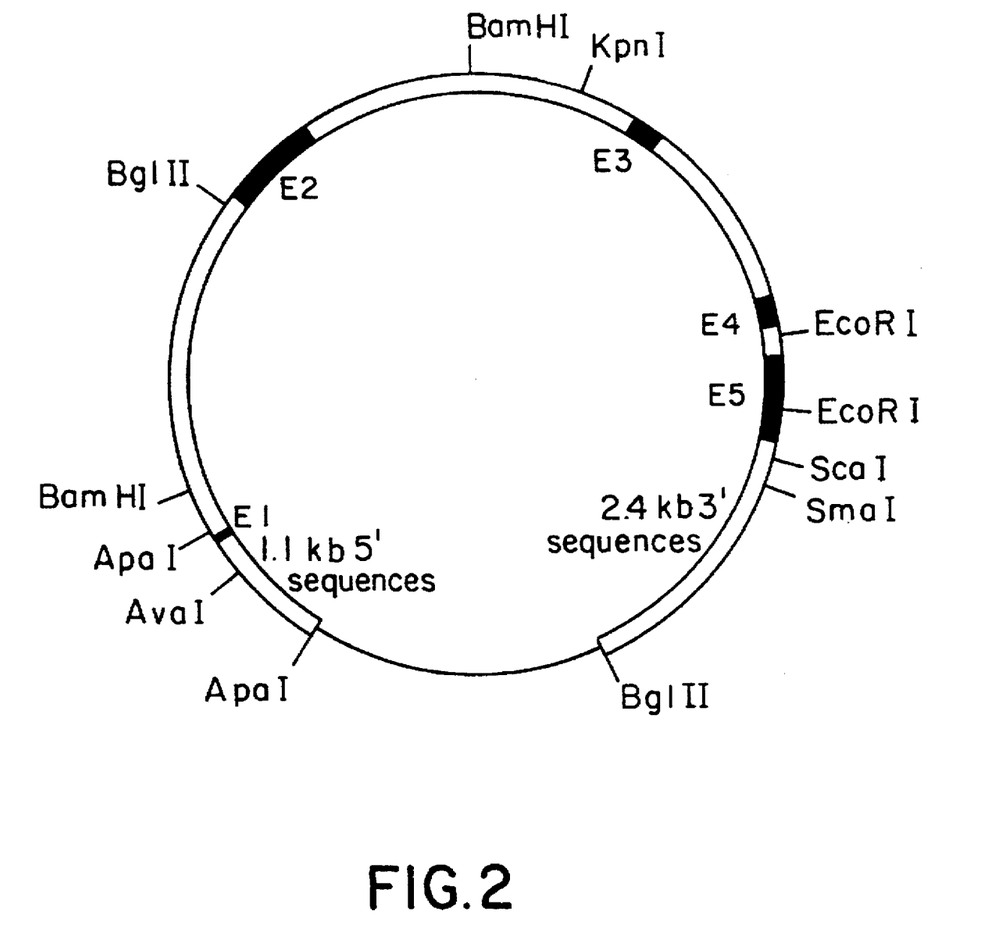
FIG. 2: Restriction Map of Plasmid pHAgTM14

The construction of the plasmid pHAgTM14 used for the production of transgenic rats is explained in the paper by Fukamizu et al., loc. cit. The restriction map of the plasmid pHAgTM14 is depicted in FIG. 2.

The 16.3 kb DNA fragment which encompasses the entire human angiotensinogen gene including the 1.1 kb of 5' flanking and 1.4 kb of 3' flanking sequences was used for the production of transgenic rats after digestion of the pUC19 vector DNA according to the method described in Example 1. The rat DNAs were, as described in Example 1, screened for the presence of transgenic angiotensinogen DNA with a radioactively labelled probe specific for human angiotensinogen.

4 rats, designated TGR(hAOGEN) 1623, 1663, 1670 and 1671, had the transgene incorporated into their genomes and transmitted it to their offspring by heredity. In the lines derived from TGR (hAOGEN) 1623 and 1670 the transgene in the F3 generation is present in homozygous form.

EXAMPLE 3

Production of Transgenic Rats Carrying the Human Renin and the Human Angiotensinogen Gene in Their Genomes Offspring of the F1 generation of TGR(hAOGEN) 1670 were cross-bred with offspring of the F1 generation of TGR (hREN) 1936. Of the 8 offspring of this cross-breed 4 did not carry any of the transgenes in their genomes; one carried the renin transgene, one the angiotensinogen transgene and 2 both transgenes.

EXAMPLE 4

Test of Tissue-Specific Expression of the Transgenes

The expression of transgenic mRNA in different tissues was examined in an "RNase Protection Assay" (Sambrook et al., loc. cit.). For the detection of the transgenic renin expression a ³²P labelled RNA transcript was produced by transcription of a 291 nucleotid antisense RNA of a pGEM4 vector subcloned SacI/EcoRV fragment derived from a human renin cDNA clone by using T7-RNA polymerase. Said transcript contains 225 nucleotides of human renin antisense RNA and 66 nucleotides of the sequence coded for by the vector.

For an assay of the transgenic angiotensinogen expression antisense RNA transcribed from a StuI/AvaII fragment of human angiotensinogen cDNA which was subcloned in the vector pGEM5 was used. For transcription T7 RNA polymerase was used. The transcript comprised 361 nucleotides of the antisense RNA and 51 nucleotides of the sequence coded for by the vector.

For hybridization with the antisense RNAs specific for human renin and angiotensinogen the entire RNA was isolated according to the method described by Auffray and Rougeon, Eur. J. Biochem. 107 (1980) 303–314 by precipitation with lithium chloride. Samples of dried RNA were dissolved in 30 µl 80% formamide, containing 40 mM PIPES (pH 6.8), 400 mM NaCl, 1 mM EDTA and $2 \times 10^5$ cpm of the gel-purified antisense transcript. After heat denaturation (60 sec. at 95° C.) and incubation at 50° C. for 20 hrs, RNase digestion was performed in 300 µl buffer containing 40 µg/ml RNase A (Sigma) and 2 µg/ml RNase T1 (Calbiochem) at 37° C. for 45 minutes.

The RNA sequences protected against the RNase digestion (hybrids from RNA and radioactively labelled probe) were analyzed after digestion of the enzymes by proteinase K in gel electrophoresis on 8M urea/5% polyacrylamide gel. After electrophoresis the gels were dried and subjected to autoradiography at −70° C.

Figure 3A:
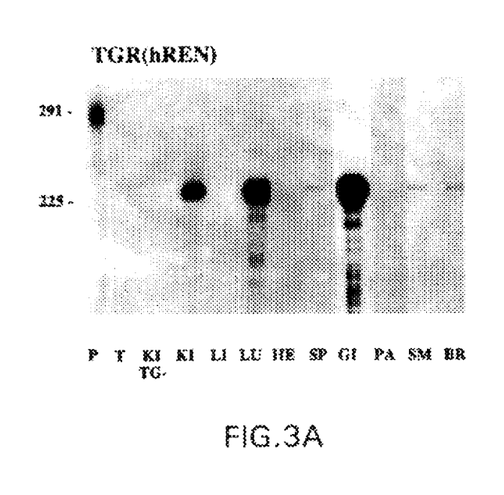
Figure 3B:
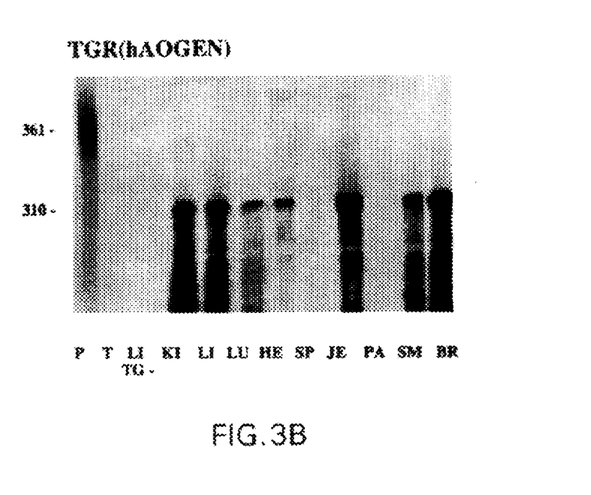
Figure 4A:
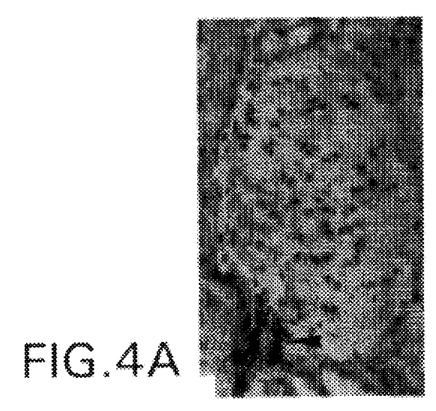
Figure 4B:
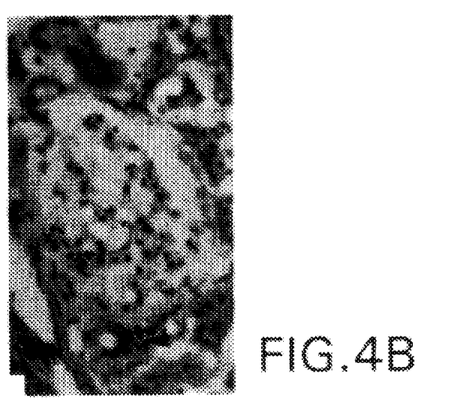
Figure 4C:
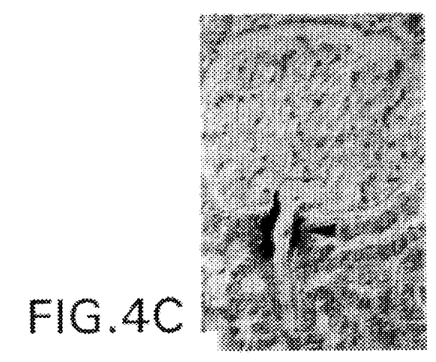
Figure 4D:
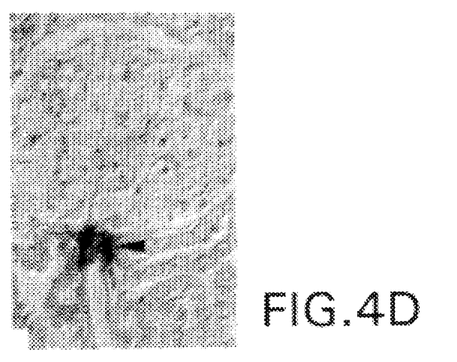
Figure 4E:
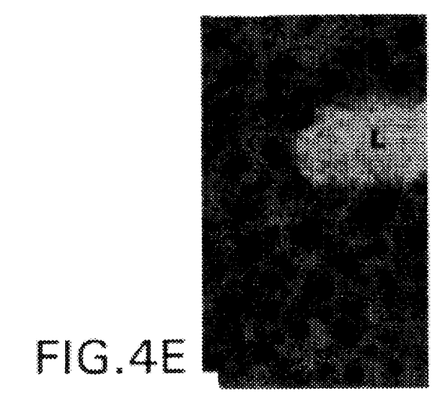
Figure 4F:
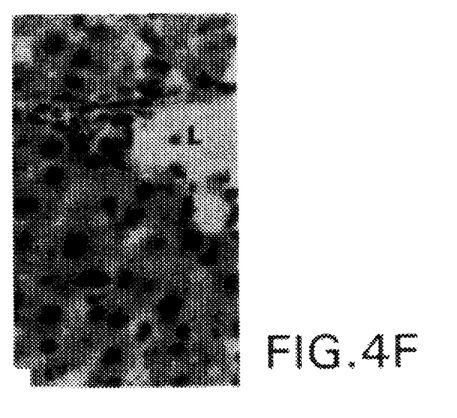

The results of this assay are depicted in FIG. 3 and summarized in Tables I and II. They show that transgenic renin mRNA is preferably expressed in the kidneys, in the lungs and in the intestines. However, no expression could be observed in the heart or in the liver. Transgenic angiotensinogen mRNA was preferably detected in the liver, the kidneys, the brain, in the heart and in the jejunum.

The transcript of transgenic renin gene detected in the kidneys by Northern blotting (Sambrook et al., loc. cit.) and subsequent .hybridization with a 298 bp ApaI/EcoRI fragment from plasmid pHag3 (Kageyama et al., loc. cit.) corresponded in its size of 16 S to the one found in human kidneys. This transcript could not be detected in non-transgenic control rats.

Expression of transgenic renin in the kidneys and of the transgenic angiotensinogen in the liver was confirmed by immunohistochemical tests and by in situ hybridization tests (FIG. 4). Furthermore, in situ hybridization tests served to prove angiotensinogen mRNA expression in the kidneys and in the brain.

For in situ hybridizations a cannula was inserted into the animals' aortae. Then the rats were fixated by perfusion with 3% paraformaldehyd in PBS for 5 minutes.

For the immunohistochemical tests the kidneys were subsequently fixated for 12 hrs and embedded in paraffin. The slices were deparaffined with a xylol/alcohol series and specific polyclonal rabbit antibodies in dilutions of 1:1,000 to 1:10,000 were applied. Bound antibody was detected with a peroxidase-antiperoxidase system using diaminobenzidine and 0.02% $H_2O_2$ (Sternberger et al., Immunochemistry (1979), John Wiley & Sons, New York). The tissues were stained with hematoxylineosine.

For in situ hybridizations the organs were washed in sucrose PBS (800 mOsmol) and shock-frozen. To detect renin mRNA expression a 330 bp SacI/PstI fragment from the mouse renin cDNA was subcloned into the vector pSP65. The recombinant plasmid was linearized by digestion with AccI and antisense RNA was prepared by transcription with T7 RNA polymerase. To detect angiotensinogen mRNA a 290 bp PvuII/BamHI fragment from rat angiotensinogen cDNA was subcloned into the vector pGEM4, the recombinant plasmid was linearized by digestion with EcoRI and antisense RNA was prepared by using Sp6-polymerase. In situ hybridizations were carried out according to the method described by Bachmann et al., Histochemistry 94 (1990), 517–523. The highest stringency in washing was 0.1×SSC at 48° C. (20 minutes). The tissue slices were counter-stained with hematoxylineosine.

The results are summarized in Table I (renin) and II (angiotensinogen).

The expression pattern for transgenic renin and transgenic angiotensinogen in rats which carry both the renin and the angiotensinogen gene corresponds for each transgene to the one found in rats carrying only one transgene.

EXAMPLE 5

Determination of the Plasma Values for Transgenic Renin and Transgenic Angiotensinogen The values for human renin in the plasma of renin transgenic rats were determined in a direct immunoradiometric assay (IRMA). 2 pairs of monoclonal antibodies were used with one pair being specific for active human renin (3E8 and 4G1 [Menard et al., J. Hypertens. Suppl. 3 (1985), 275–278] and the other pair being specific for entire renin (3E8 and 4E1 [Toffelmire et al., J. Clin. Invest. 83 (1989), 679–687]).

250 µl rat plasma was mixed with about 20 mg Magnogel (Pasteur, France) to which the monoclonal antibody 3E8 was coupled by standard techniques. 3E8 recognizes both active renin and prorenin which together are designated entire renin. The samples were incubated at room temperature for 2 hrs on a magnelio shaker (Pasteur, France). Then 2 ml washing buffer (0.002M imidazol containing 0.1% horse serum, 0.0001% $NaN_3$ and 0.001% dye) was added for 2 minutes. The magnogel was fixated by way of a magnet, the supernatant was discarded. After a second washing step 250 µl (250,000 cpm) of $^{125}J$ labelled monoclonal antibody 4G1 for the assay of active human renin (the antibody binds to the active center of the enzyme) or 250 µl (250,000 cpm) of $^{125}J$ labelled monoclonal antibody 4E1 for the assay of entire renin were added. After 3 hrs incubation at room temperature the samples were washed three times as described above.

The samples were evaluated for 2 minutes in a gamma counter (Berthold, FRG). Rat renin concentration was determined as described by Schelling et al., loc. cit. and Hermann et al., loc. cit.

The results are summarized in Table I.

High plasma values for human renin were detected in renin transgenic rats but not in non-renin transgenic rats. In the rat TGR (hREN) 1988 the value for active renin was 226 pg/ml, in the rat TGR (hREN) 1936 it was 4.9 pg/ml. The average human renin activity in rat plasma is 18 ng ANG I/ml/h. The average value in the human plasma is 25.1 ng ANG I/ml/h, i.e., it has the same range. The values for rat prorenin and rat renin were unchanged in comparison to non-transgenic control rats.

The values for angiotensinogen, angiotensin I and angiotensin II of renin transgenic rats do not significantly differ in comparison to non-transgenic control rats. This shows that rat angiotensinogen is not cleaved by human renin.

The angiotensinogen values in the plasma were determined in an ELISA test. The wells of "Immunoplates" (STL, Overath, FRG) were incubated at 4° C. for 16 hrs with 100 µl of the monoclonal antibody $H_{10}F_{10}$ (0.5 µg/ml) which is specific for human angiotensinogen.

The further steps were carried out at room temperature. After three washing steps with PBS (phosphate buffered saline) containing 0.5% Tween 20® the free binding sites on the plates were blocked for 1 hr with 200 µl BSA solution (in the above described PBS Tween buffer). The plates were washed three times as described above. The wells were then diluted with 100 µl of the plasma samples each and incubated for 2 hrs.

After 3 further washing steps the wells were incubated for 2 hrs with 100 µl of a 1:2,000 dilution in PBS-Tween of the polyclonal rabbit antibody 4H69.6 specific for human angiotensinogen (Hilgenfeldt et al., Eur. J. Clin. Pharmacol. 38 (1990), 125–131). The plates were thoroughly washed and peroxidase-coupled goat anti-rabbit IgG (Sigma, Munich) which was prepared according to the producer's information was added to the wells and incubated for 2 hrs.

After further 5 washing steps the staining reaction was started by addition of an o-phenylene diamine solution in sodium phosphate buffer (0.1M, pH 7.5) containing 6.5M $H_2O_2$. The enzymatic reaction was interrupted after 10 minutes by adding 100 µl 12% $H_2SO_4$.

The staining reaction was measured at 492 nm with an "ELISA-Reader EAR 400" (SLT-Labinstruments, Austria). Rat angiotensinogen was indirectly determined after incubation of plasma with pig renin (1 h at 37° C.). The amount of angiotensin I was measured via an ANG I-RIA (Hermann et al., loc. cit.). The total amount of ANG I corresponds to the amount of rat angiotensinogen. The results for the animals of lines 1663 and 1670 are summarized in Table II. The values represent the average value and the standard deviation for 6 animals for each measurement.

The plasma values for angiotensinogen were increased in all 4 angiotensinogen transgenic rats and ranged from 125 µg/ml (1671) to 3,000 µg/ml (1623). In non-transgenic control rats no human angiotensinogen was found in the plasma. The plasma values for rat prorenin, rat renin, rat angiotensin I, rat angiotensin II and rat CE were not influenced by the expression of the angiotensinogen transgene. This result proves that human angiotensinogen, even at high plasma concentrations, is no substrate for rat renin.

EXAMPLE 6

Influence of Sodium Depletion on the Renin Values in the Plasma by the Administration of Furosemide Sodium depletion in rats was carried out by intraperitoneal injection of 120 mg/kg body weight furosemide and a simultaneous low-salt diet of 10 mOsmol/day for seven days. The blood samples were recovered prior to the begin of the sodium depletion and seven days after treatment by retroorbital puncture with a mild ether anaesthesia.

Figure 5A:
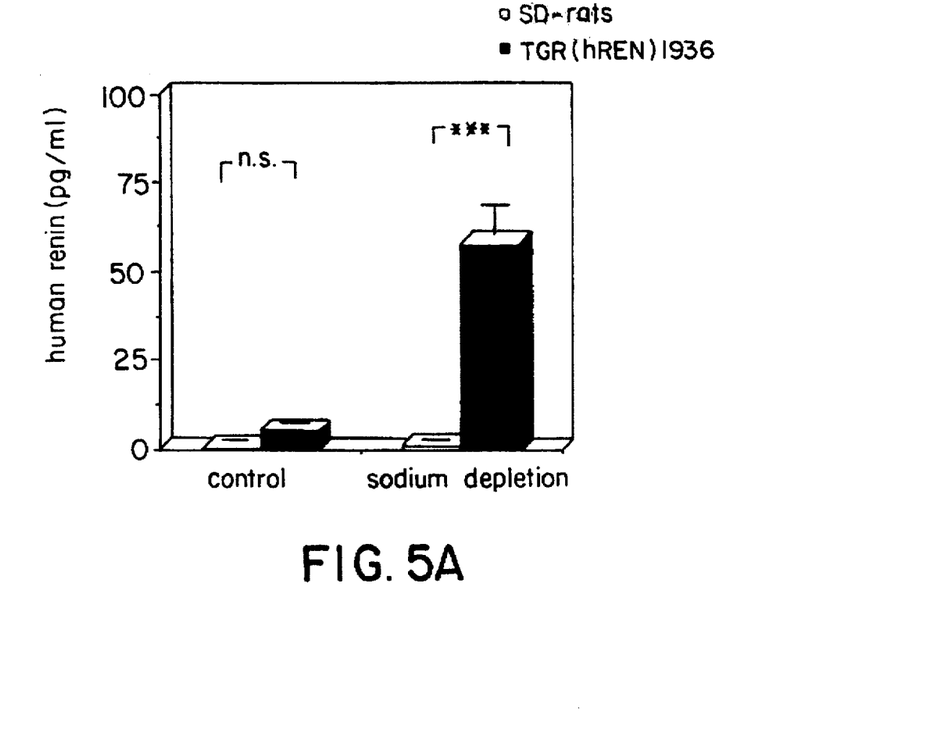
Figure 5B:
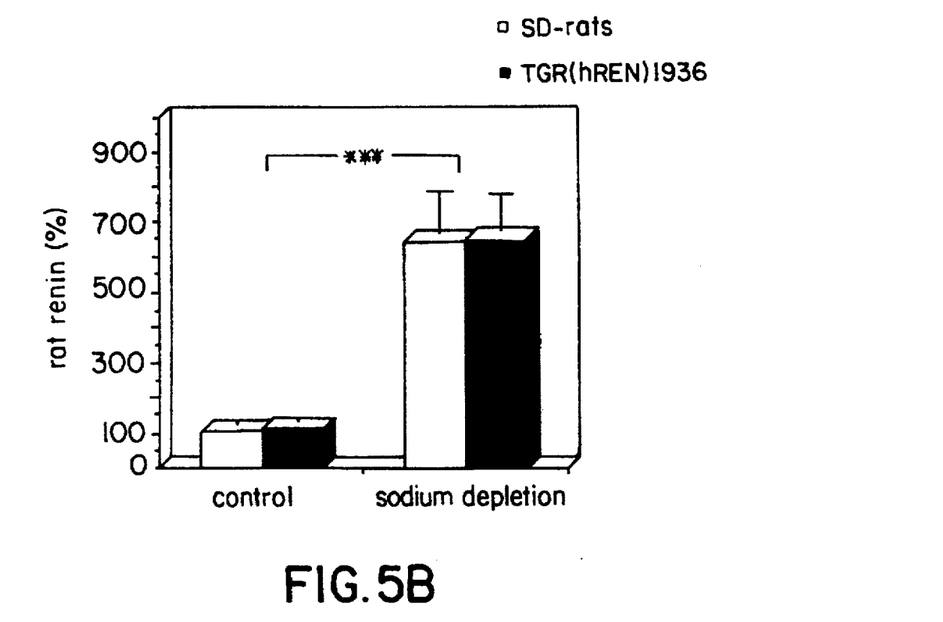

The results of these tests are depicted in FIG. 5. They show that the transgenic renin level in the plasma of renin transgenic rat increases by about factor 10 after sodium depletion. An increase of the endogenous renin values by a factor 5 was observed both in renin transgenic and in non-transgenic rats after sodium depletion. The increase of the values for transgenic renin did not influence the endogenous angiotensinogen values. This is further evidence for the species-specificity of the tested RAS systems. Animals with increased transgenic renin level can be used for a sensitive assay for the reaction and testing of inhibitors of the renin-angiotensin system after infusion of human angiotensinogen.

Figure 6:
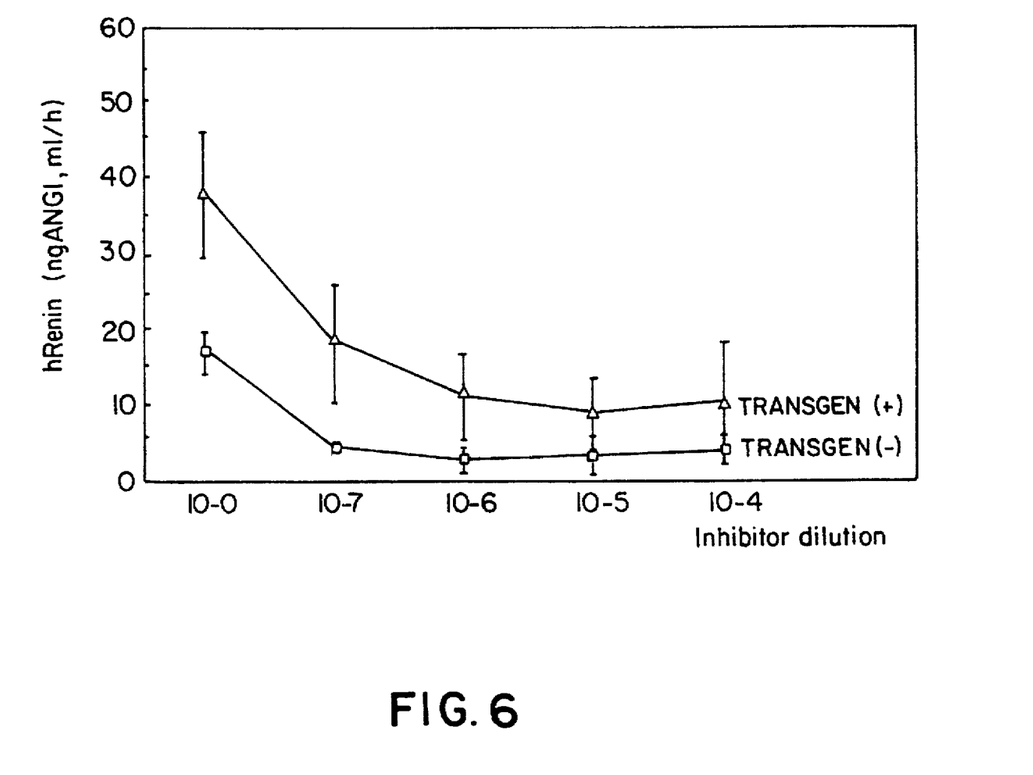
FIG. 6: Specific Inhibition of Transgenic Renin in the Plasma of Renin Transgenic Rats by an Inhibitor Specific for Human Renin The inhibitor RO425892 specific for human renin was incubated in concentrations of $10^{-8}$M to $10^{-4}$M with plasma of TGR(hREN) transgenic rats. The diagram shows that human renin is completely inhibited at an inhibitor concentration of $10^{-6}$. The inhibitor does not react with rat renin.

In a further test the plasma of the renin transgenic rat TGR(hREN)1936 was incubated after sodium depletion wit the inhibitor RO425892 specific for human renin. Said incubation led to a complete inhibition of transgenic renin activity at an inhibitor concentration of $10^{-6}$ but had no effect on the activity of the endogenous renin (FIG. 6). These results support the in vivo findings and permit in vivo—in vitro analogous analysis.

EXAMPLE 7

Determination of the Blood Pressure in Renin and/ or Angiotensinogen Transgenic Rats The blood pressure of rats was measured in two different ways:

1. Tail-plethysmographically: the rats were slightly narcotised with ether. The rat's tail is introduced into a plethysmographic tube and pressure is increased within the tubular system by way of a manometer. As soon as the systolic blood pressure is higher than the plethysmographic pressure it can be read on a water column.
2. For direct measurement of arterial blood pressure the arteria femoralis is laid open. A polyethylene tube is introduced into the arteria femoralis and fastened. The polyethylene tube is filled with an anticoagulant heparin solution and connected to a blood pressure converter which converts the pressure into electric pulses. The latter are recorded by an electronic recorder. A more detailed description of this method can be found in Rasches et al., "Hypertensive Mechanism", F. K. Schattauer Verlag, Stuttgart-New York, 1982, page 779–797 and the references described therein.

The measurement of the blood pressure in transgenic rats which either carry only the renin transgene or only the angiotensinogen gene in their genomes showed that the blood pressure was in the normal range of 90 mm Hg diastolic and 140 mm Hg systolic. Rats which carried both genes in their genomes temporarily exhibited an increased blood pressure of about 155 mm Hg systolic.

The blood pressure was measured intraarterially after a catheter had been placed into the arteria femoralis of a conscious, free-moving animal (direct arterial measuring of the blood pressure).

EXAMPLE 8

Influence of the Inhibitor RO425892 Specific for Human Renin and of the Angiotensin Receptor Antagonist DUP 753 on the Blood Pressure of Renin Transgenic Rats RO425892 was administered to renin transgenic rats in a concentration of 1000 µg/kg body weight after sodium depletion. Administration of the inhibitor had no effect on the blood pressure. This result, too, serves to prove that human renin does not react with rat angiotensinogen.

In a further test renin transgenic rats received an infusion wit the angiotensin receptor antagonist DUP 753 (10 mg/kg body weight) after sodium depletion. As a result of this infusion blood pressure was reduced by ±15 mm Hg since DUP 753 reacts both with the human and the rat RAS.

EXAMPLE 9

Figure 7A:
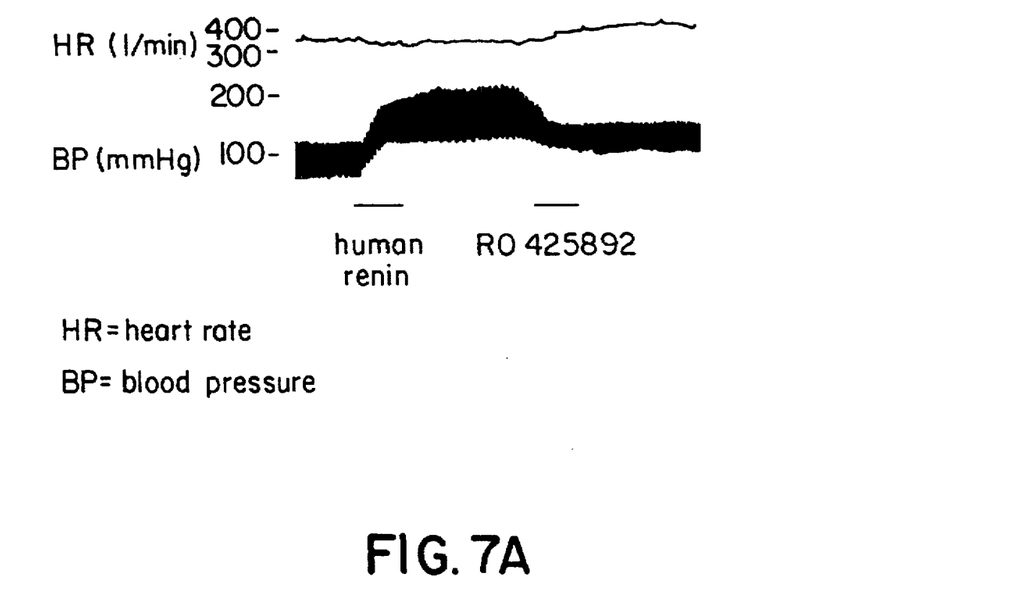
Figure 7B:
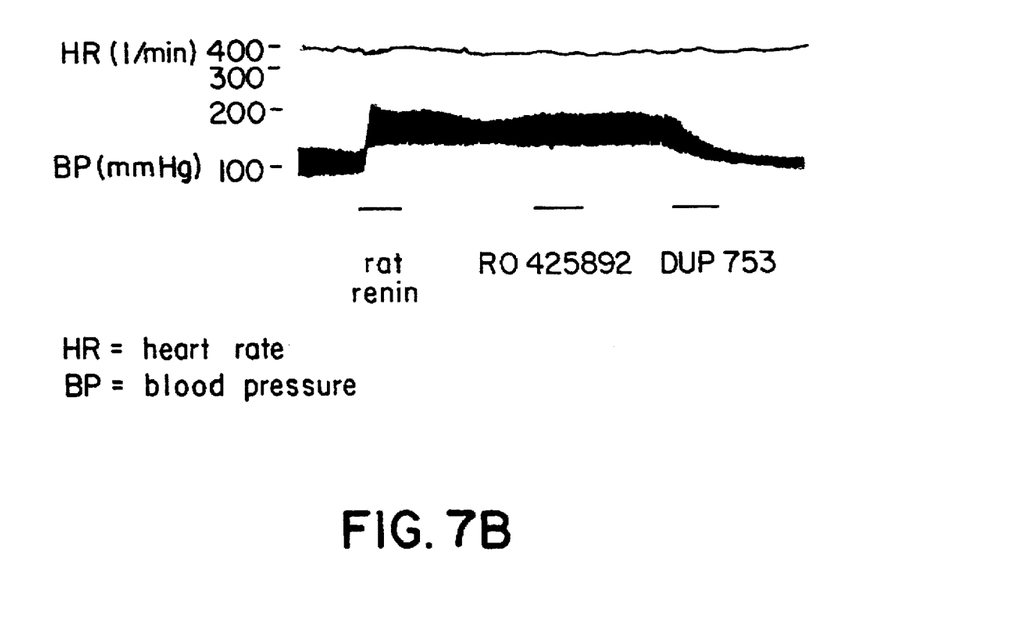
Figure 8A:
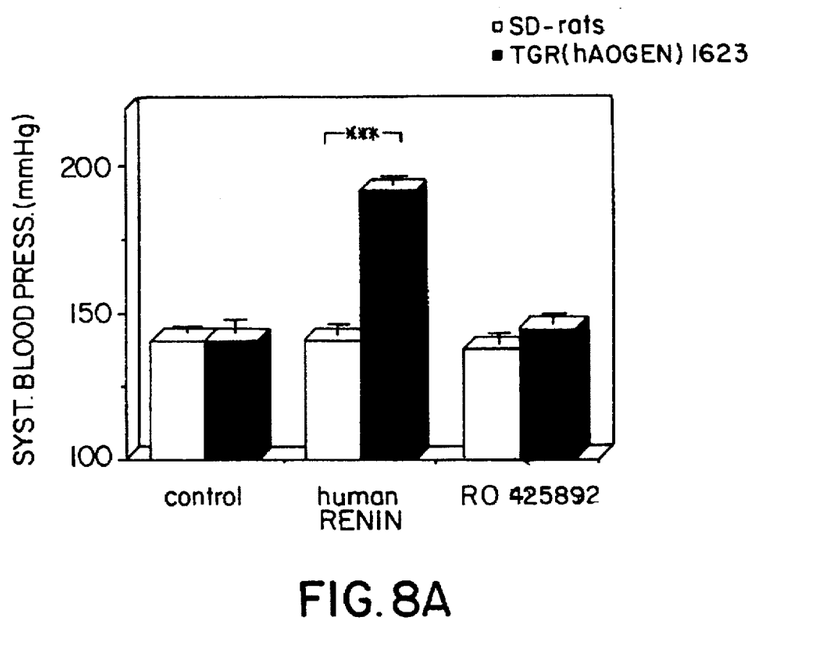
Figure 8B:
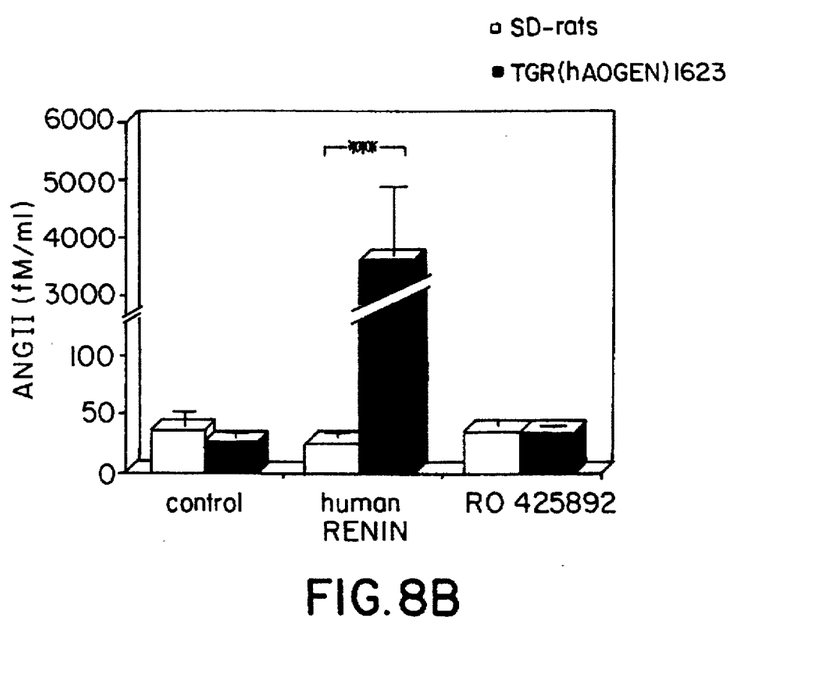

Influence of the Administration of Human Renin on the Blood Pressure of Angiotensinogen Transgenic Rats Angiotensinogen transgenic rats 1623 and 1670 were intravenously administered purified human kidney renin and recombinant human renin in a concentration of 5 μg ANG I/ml/h. The renin administration led to a dose-related increase in the systolic blood pressure (FIGS. 7 and 8).

The above increase in blood pressure could be obviated by oral or intravenous pretreatment of angiotensinogen transgenic rats with the inhibitor RO425892 specific for human renin which was administered in an amount of 1.5 mg/kg body weight.

The administration of rat renin likewise led to increased blood pressure values in these rats but the increase could not be obviated by administering the inhibitor RO425892 specific for human renin. The blood pressure increase after administration of rat renin could, however, be reversed by administering the substance Captopril (does not act species-specific) which inhibits the converting enzyme and the angiotensin II receptor antagonist DUP 753 (likewise does not react species-specific).

In non-transgenic control rats an increase in blood pressure could only be observed when rat renin was administered but not when human renin was administered.

Infusion of rat renin increases the blood pressure in non-transgenic rats by species-specific interaction with endogenous angiotensinogen. Human renin, however, does not react with rat angiotensinogen and therefore does not lead to increased blood pressure.

TABLE I

|  | control | TGR(hREN) 1936 | TGR(hREN) 1988 |
| --- | --- | --- | --- |
| plasma RAS |  |  |  |
| active human renin (pg/ml) | 0.4 ± 0.3 | 4.9 ± 1.13 | 226.0 ± 0.7 |
| total human renin (pg/ml) | 0.0 ± 0.0 | 129.9 ± 17.8 | 6820 ± 290 |
| rat renin (ng ANG I/ml*h) | 51.4 ± 11.9 | 58.9 ± 16.9 | 45.5 ± 4.3 |
| tissue mRNA |  |  |  |
| kidney | – | ++ | +++ |
| adrenals | – | – | + |
| lung | – | ++ | +++ |
| heart | – | – | – |
| intestines | – | ++ | +++ |
| spleen | – | + | ++ |
| liver | – | – | – |
| thyroid | – | + | ++ |
| thymus | – | + | ++ |
| brain | – | – | + |
| medulla | – | – | + |
| hypothalamus | – | – | + |

Expression of the human renin gene was detected by RNase protection assays (cf. Example 4).
The signal strength obtained was designated with the following symbols:
(–)negative
(+)weak
(++)medium
(+++)strong

TABLE II

|  | control | TGR(hAOGEN) 1663 | TGR(hAOGEN) 1670 |
| --- | --- | --- | --- |
| plasma RAS |  |  |  |
| human AOGEN (μg/ml) | 0.0 ± 0.0 | 465.3 ± 44.8 | 397.4 ± 33.4 |
| rat AOGEN (μg/ml) | 21.2 ± 5.8 | 28.5 ± 2.18 | 30.3 ± 0.8 |

TABLE II-continued

|  | control | TGR(hAOGEN) 1663 | TGR(hAOGEN) 1670 |
| --- | --- | --- | --- |
| ANG I (fM/ml) | 444.9 ± 177.5 | 507.6 ± 108.6 | 281.6 ± 159.2 |
| ANG II (fM/ml) | 30.5 ± 11.1 | 48.2 ± 6.5 | 42.6 ± 0.8 |
| tissue mRNA |  |  |  |
| liver | – | +++ | +++ |
| kidney | – | ++ | ++ |
| lung | – | + | + |
| pancreas | – | – | – |
| jejunum | – | ++ | ++ |
| heart | – | ++ | ++ |
| spleen | – | – | – |
| brain | – | + | ++ |
| SMG * | – |  | + |

* submandibular gland
Expression of the human angiotensinogen gene was detected by RNase protection assays (cf. Example 4).
The signal strength obtained was designated with the following symbols:
(–)negative
(+)weak
(++)medium
(+++)strong
AOGEN = angiotensinogen

We claim:

1. A transgenic rat containing in its genome at least one transgene encoding human renin and at least one transgene encoding human angiotensinogen; wherein said rat expresses human renin and human angiotensinogen at a level sufficient to produce a blood pressure of at least 90 mm Hg diastolic pressure and at least 140 mm Hg systolic pressure.

2. A transgenic rat according to claim 1, wherein said rat presents with a blood pressure of at least 155 mm Hg systolic pressure.

3. A transgenic rat according to claim 1, wherein said rat presents with a blood pressure of at least 160 mm Hg systolic pressure.

4. A transgenic rat containing in its genome at least one transgene encoding human renin and at least one transgene encoding human angiotensinogen; wherein said rat expresses human renin and human angiotensinogen at a level sufficient to produce a blood pressure of at least 90 mm Hg diastolic pressure and at least 140 mm Hg systolic pressure; and wherein an least one of said transgenes is expressed from a heterologous promoter.

5. A transgenic rat according to claim 4, wherein said rat presents with a blood pressure of at least 155 mm Hg systolic pressure.

6. A transgenic rat according to claim 4, wherein said rat presents with a blood pressure of at least 160 mm Hg systolic pressure.

7. A transgenic rat according to claim 4, wherein said rat presents with a blood pressure of at least 95 mm Hg diastolic pressure.

8. A transgenic rat according to claim 4, wherein said rat presents with a blood pressure of at least 95 mm Hg diastolic pressure and at least 160 mm μg systolic pressure.

9. A transgenic rat according to claim 4, wherein both of said transgenes are expressed from heterologous promoters.

10. A transgenic rat according to claim 9, wherein said rat presents with a blood pressure of at least 155 mm Hg systolic pressure.

11. A transgenic rat according to claim 9, wherein said rat presents with a blood pressure of at least 160 mm Hg systolic pressure.

12. A transgenic rat according to claim 9, wherein said rat presents with a blood pressure of at least 95 mm Hg diastolic pressure.

13. A transgenic rat according to claim 9, wherein said rat presents with a blood pressure of at least 95 mm Hg diastolic pressure and at least 160 mm Hg systolic pressure.

14. A transgenic rat containing in its genome at least one transgene encoding human angiotensinogen; wherein said rat expresses human angiotensinogen at a level sufficient to produce a blood pressure of at least 90 mm Hg diastolic pressure and about 200 mm Hg systolic pressure when human renin is administered to said rat.

15. A transgenic rat according to claim 14, wherein said transgene is expressed from a heterologous promoter.

* * * * *